US012605362B2

(12) United States Patent
Chapela Duarte Pires et al.

(10) Patent No.: US 12,605,362 B2
(45) Date of Patent: Apr. 21, 2026

(54) ELETRIPTAN HYDROBROMIDE FOR TREATMENT OF SPINAL CORD INJURY AND IMPROVEMENT OF LOCOMOTOR FUNCTION

(71) Applicants: TECHNOPHAGE, INVESTIGAÇÃO E DESENVOLVIMENTO EM BIOTECNOLOGIA, S.A., Lisbon (PT); INSTITUTO DE MEDICINA MOLECULAR JOÃO LOBO ANTUNES, Lisbon (PT)

(72) Inventors: Diana Sofia Chapela Duarte Pires, Lisbon (PT); Sofia Marisa Volker Côrte-Real, Lisbon (PT); Maria Leonor Tavares Saúde, Lisbon (PT); Isaura Vanessa Antunes Martins, Lisbon (PT); Sara Cristina Mauricio De Sousa, Lisbon (PT)

(73) Assignees: TECHNOPHAGE, INVESTIGAÇÃO E DESENVOLVIMENTO EM BIOTECNOLOGIA, S.A., Lisbon (PT); FUNDAÇÃO GIMM—GULBENKIAN INSTITUTE FOR MOLECULAR MEDICINE, Lisbon (PT)

( * ) Notice: Subject to any disclaimer, the term of this patent is extended or adjusted under 35 U.S.C. 154(b) by 852 days.

(21) Appl. No.: 17/794,595

(22) PCT Filed: Dec. 21, 2020

(86) PCT No.: PCT/IB2020/062306
§ 371 (c)(1),
(2) Date: Jul. 21, 2022

(87) PCT Pub. No.: WO2021/148868
PCT Pub. Date: Jul. 29, 2021

(65) Prior Publication Data
US 2023/0346746 A1 Nov. 2, 2023

(30) Foreign Application Priority Data
Jan. 22, 2020 (PT) ........................................ 116069

(51) Int. Cl.
*A61K 31/4045* (2006.01)
*A61P 25/28* (2006.01)

(52) U.S. Cl.
CPC .......... *A61K 31/4045* (2013.01); *A61P 25/28* (2018.01)

(58) Field of Classification Search
CPC .................................................. A61K 31/4045
USPC ...................................................... 514/414
See application file for complete search history.

(56) References Cited

U.S. PATENT DOCUMENTS

2013/0274235 A1* 10/2013 Isacson .............. A61K 31/4178
506/10

FOREIGN PATENT DOCUMENTS

WO 199206973 A1 4/1992
WO WO-2008024930 A2 * 2/2008 .............. A61P 25/00

OTHER PUBLICATIONS

Thapa et al., Lumbar Plexopathy Secondary to Spontaneous Large Retroperitoneal Hematoma, The American Journal of Medicine, 2016, vol. 129(12), pp. 1-2 (Year: 2016).*
Zhang Bei et al, "Reducing age-dependent monocyte-derived macrophage activation contributes to the therapeutic efficacy of NADPH oxidase inhibition in spinal cord injury", Brain, Behavior and Immunity, vol. {0} 76, Feb. 1, 2019 (Feb. 1, 2019), p. 139-150.
Kjell, J. & Olson, L. Rat models of spinal cord injury: from pathology to potential therapies. Dis Model Mech 9, 1125-1137, doi:10.1242/dmm. 025833 (2016).
Boutonnet, M., Laemmel, E., Vicaut, E., Duranteau, J. & Soubeyrand, M. Combinatorial therapy with two pro•coagulants and one osmotic agent reduces the extent of the lesion in the acute phase of spinal cord injury in the rat. Intensive Care Med Exp 5, 51, doi:10.1186/s40635-017-0164-z (2017).
Donovan, J. & Kirshblum, S. Clinical Trials in Traumatic Spinal Cord Injury. Neurotherapeutics 15, 654-668, doi:10.1OO7/s13311-018-0632-5 (2018).
Duncan, G. J. et al. Locomotor recovery following contusive spinal cord injury does not require oligodendrocyte remyelination. Nat Commun 9, 3066, doi: 10.1038/s41467-018-05473-1 (2018).
Zhou, X., He, X. & Ren, Y. Function of microglia and macrophages in secondary damage after spinal cord injury. Neural Regen Res 9, 1787-1795, doi: 10.4103/1673-5374.143423 (2014).
(Continued)

*Primary Examiner* — Jeffrey H Murray
*Assistant Examiner* — Rilla Marie Samsell
(74) *Attorney, Agent, or Firm* — Ballard Spahr LLP

(57) ABSTRACT

The present invention discloses the use of Eletriptan Hydrobromide in the treatment of spinal cord injury and improvement of the locomotive function. Despite the major efforts done in attempting to improve the limited recovery upon injury, only a multi-target combinatorial therapeutic approach should be effective for the complexity of spinal cord injury nature. Taking advantage of a larval zebrafish drug discovery platform it is identified herein that Eletriptan Hbr has locomotor recovery properties in a pro-regenerative model and it has been confirmed to have conservative effect on a rodent (pro-fibrotic) contusion model. This approach allowed to identify a promising new therapeutic indication for Eletriptan Hbr, which associated with a combinatorial therapeutic strategy and innovative engineering approaches, shows great potential for spinal cord injury recovery.

11 Claims, 8 Drawing Sheets

(56)                References Cited

OTHER PUBLICATIONS

Yilmaz, T. & Kaptanoglu, E. Current and future medical therapeutic strategies for the functional repair of spinal cord injury. World J Orthop 6, 42-55, doi: 10.5312/wjo.v6.i1.42 (2015).

Picoli, C. C. et al. Pericytes Act as Key Players in Spinal Cord Injury. Am J Pathol 189, 1327-1337, doi:10.1016/j.ajpath.2019.03. 008 (2019).

O'Shea, T. M., Burda, J. E. & Sofroniew, M. V. Cell biology of spinal cord injury and repair. J Clin Invest 127, 3259-3270, doi:10. 1172/JCI90608 (2017).

Gaudet, A. D. & Fonken, L. K. Glial Cells Shape Pathology and Repair After Spinal Cord Injury. Neurotherapeutics 15, 554-577, doi:10.1007/s13311-018-0630-7 (2018).

Hausmann, 0. N. Post-traumatic inflammation following spinal cord injury. Spinal Cord 41, 369-378, doi: 10.1038/sj.sc.3101483 (2003).

Bradbury, E. J. & Burnside, E. R. Moving beyond the glial scar for spinal cord repair. Nat Commun 10, 3879, doi:10.1038/s41467-019-11707-7 (2019).

Orr, M. B. & Gensel, J. C. Spinal Cord Injury Scarring and Inflammation: Therapies Targeting Glial and Inflammatory Responses. Neurotherapeutics 15, 541-553, doi:10.1007/s13311-018-0631-6 (2018).

Cregg, J.M. et al. Functional regeneration beyond the glial scar. Exp Neurol 253, 197-207, doi:10.1016/j .expneurol.2013.12.024 (2014).

Keirstead, H. S. et al. Human embryonic stem cell-derived oligodendrocyte progenitor cell transplants remyelinate and restore locomotion after spinal cord injury. J Neurosci 25, 4694-4705, doi:10.1523/JNEUROSCI.0311-05.2005 (2005).

McTigue, D. M. & Tripathi, R. B. The life, death, and replacement of oligodendrocytes in the adult CNS. J Neurochem 107, 1-19, doi:10.1111/j.1471-4159.2008.05570.x (2008).

Bellver-Landete, V. et al. Microglia are an essential component of the neuroprotective scar that forms after spinal cord injury. Nat Commun 10, 518, doi:10.1038/s41467- 019-08446-0 (2019).

Anderson, M. A. et al. Astrocyte scar formation aids central nervous system axon regeneration. Nature 532, 195-200, doi:10.1038/ naturel 7623 (2016).

Courtine, G. & Sofroniew, M. V. Spinal cord repair: advances in biology and technology. Nat Med 25, 898-908, doi:10.1038/s41591-019-0475-6 (2019).

Hall, C. J. et al. Repositioning drugs for inflammatory disease—fishing for new anti-inflammatory agents. Dis Model Mech 7, 1069-1081, doi: 10.1242/dmm.016873 (2014).

Rennekamp, A. J. & Peterson, R. T. 15 years zebrafish chemical screening. Curr Opin Chem Biol 24, 70, doi: 10.1016/j .cbpa.2014. 10.025 (2015).

Early, J. J. et al. An automated high-resolution in vivo screen in zebrafish to identify chemical regulators of myelination. Elife 7, doi:10.7554/eLife.35136 (2018).

MacRae, C. A. & Peterson, R. T. Zebrafish as tools for drug discovery. Nat Rev Drug Discov 14, 721-731, doi:10.1038/nrd4627 (2015).

Capi, M. et al. Eletriptan in the management of acute migraine: an update on the evidence for efficacy, safety, and consistent response. Ther Adv Neurol Disord 9, 414-423, doi:10.1177/1756285616650619 (2016).

Tepper, S. J., Rapoport, A. M. & Sheftell, F. D. Mechanisms of action of the 5-HTIB/ID receptor agonists. Arch Neurol 59, 1084-1088, doi: 10.1001/archneur.59.7.1084 (2002).

Chapela, D. et al. A zebrafish drug screening platform boosts the discovery of novel therapeutics for spinal cord injury in mammals. Sci Rep 9, 10475, doi:10.1038/s41598- 019-47006-w (2019).

De Esch, C. et al. Locomotor activity assay in zebrafish larvae: influence of age, strain and ethanol. Neurotoxicol Teratol 34, 425-433, doi:10.1016/j.ntt.2012.03.002 (2012).

Tep, C. et al. Oral administration of a small molecule targeted to block proNGF binding to p75 promotes myelin sparing and functional recovery after spinal cord injury. J Neurosci 33, 397-410, doi: 10.1523/JNEUROSCI.0399-12.2013 (2013).

Nair, A. B. & Jacob, S. A simple practice guide for dose conversion between animals and human. J Basic Clin Pharm 7, 27-31, doi:10. 4103/0976-0105.177703 (2016).

Basso, D. M. et al. Basso Mouse Scale for locomotion detects differences in recovery after spinal cord injury in five common mouse strains. J Neurotrauma 23, 635-659, doi: 10.1089/neu.2006. 23.635 (2006).

Deuis, J. R., Dvorakova, L. S. & Vetter, I. Methods Used to Evaluate Pain Behaviors in Rodents. Front Mol Neurosci 10, 284, doi:10. 3389/fnmol.2017.00284 (2017).

Golden, J. P. et al. RET signaling is required for survival and normal function of nonpeptidergic nociceptors. J Neurosci 30, 3983-3994, doi:10.1523/JNEUROSCI.5930-09.2010 (2010).

Ma, M., Basso, D. M., Walters, P., Stokes, B. T. & Jakeman, L. B. Behavioral and histological outcomes following graded spinal cord contusion injury in the C57BI/6 mouse. Exp Neurol 169, 239-254, doi: 10.1006/exnr.2001.7679 (2001).

Hoschouer, E. L., Finseth, T., Flinn, S., Basso, D. M. & Jakeman, L. B. Sensory stimulation prior to spinal cord injury induces post-injury dysesthesia in mice. J Neurotrauma 27, 777-787, doi:10. 1089/neu.2009.1182 (2010).

Dias, D. 0. et al. Reducing Pericyte-Derived Scarring Promotes Recovery after Spinal Cord Injury. Cell 173, 153-165. e122, doi:10. 1016/j .cell.2018.02.004 (2018).

Brennan, F. H., Hall, J. C. E., Guan, Z. & P.G., P. Microglia limit lesion expansion and promote functional recovery after spinal cord injury in mice. Cold Spring Harbor Laboratory, doi:https://doi.org/ 10.1101/410258 (2018).

Brenner, D. S., Golden, J. P. & Gereau, R. W. A novel behavioral assay for measuring cold sensation in mice. PLoS One 7, e39765, doi:10.1371/journal.pone.0039765 (2012).

Oudega, M. Molecular and cellular mechanisms underlying the role of blood vessels in spinal cord injury and repair. Cell Tissue Res 349, 269-288, doi: 10• 10 07/s0 0441-012-1440-6 (2012).

Zhu, Y. et al. Hematogenous macrophage depletion reduces the fibrotic scar and increases axonal growth after spinal cord injury. Neurobiol Dis 74, 114-125, doi: 10.1016/j.nbd.2014.10.024 (2015).

Khennouf, L. et al. Active role of capillary pericytes during stimulation-induced activity and spreading depolarization. Brain 141, 2032-2046, doi:10.1093/brain/awy143 (2018).

Li, Y. et al. Pericytes impair capillary blood flow and motor function after chronic spinal cord injury. Nat Med 23, 733-741, doi:10.1038/ nm.4331 (2017).

Anastasiou et al. Prehistoric schistosomiasis parasite found in the Middle East, Published Online Jun. 20, 2014 http://dx.doi.org/10. 1016/S1473-3099(14)70794-7 (2 pages).

* cited by examiner

A

A′

A

B

Distance from epicentre

ELETRIPTAN HYDROBROMIDE FOR TREATMENT OF SPINAL CORD INJURY AND IMPROVEMENT OF LOCOMOTOR FUNCTION

CROSS REFERENCE TO RELATED APPLICATIONS

This Application is a national phase application under 35 U.S.C. § 371 of International Application No. PCT/IB2020/062306, filed Dec. 21, 2020, which claims priority to Portuguese Application No. 116069, filed Jan. 22, 2020, the contents of which are hereby incorporated by reference in their entireties.

TECHNICAL FIELD

The present invention concerns the use of Eletriptan Hydrobromide in the treatment of spinal cord injury and improvement of the locomotive function.

BACKGROUND ART

Leading to motor, sensory and autonomic dysfunction, spinal cord injury (SCI) causes a neurological trauma that affects millions of people worldwide, becoming urgent to develop effective spinal cord repair strategies for clinical use[1]. The pathophysiology of SCI can be divided into primary and secondary mechanisms of injury. The primary injury occurs due to mechanical disruption of the spinal cord tissues that induces alterations in axons, blood vessels and cell membranes, leading to an immediate neural tissue loss and demyelination[2-4]. After initial trauma took place, secondary injury occurs due to several mechanisms, namely, the blood spinal cord barrier (BSCB) disruption that leads to the infiltration of inflammatory cells, the release of inflammatory cytokines and the disproportionate release of excitatory neurotransmitters leading to excitotoxicity and ischemia[2,3,5,6]. Therefore, the secondary damage is multifactorial and characterized by the presence of inflammation that may cause reactive gliosis, edema, glial/axon scarring, and central cavitation[5-7].

A mature SCI lesion displays three main tissue compartments: a lesion core/fibrotic scar with non-neural tissue, an astrocytic scar surrounding the lesion core and a surrounding area with spared neural tissue that is functional but reactive[8]. Actually, SCI scar leads to reparative responses (that are essential to prevent the spread of cellular damage) and deleterious responses (which limit regrowth and tissue repair) that change over time and are defined by spatial location regarding to lesion[9,10,11,12]. Indeed, after injury, reactive astrocytes not only form a glial scar that limits the expansion of the lesion, confining inflammation to the lesion epicentre, as limit and inhibit axon regeneration[9,13]. Furthermore, microglia/macrophages enable phenotypic plasticity and also produce cytotoxic factors that cause a prolonged and exaggerated pro-inflammatory response which worsen the lesion damage (i.e. secondary damage)[9,14]. In addition, oligodendrocytes and oligodendrocyte precursor cells (OPCs) may die by apoptosis or necrosis but also achieve differentiation and remyelination[9,15,16]. Thus, given the complex interplay between multiple different cell types, intracellular and extracellular microenvironment, abolition of one of these cell types or completely responses is not effective for SCI repair[9,17,18]. Combinatorial therapeutic and time-dependent strategies are needed to preserve the beneficial properties of the SCI scar, improving its reparative responses, while targeting the negative facets[9,11,19].

Treatment options, either standard of care or experimental, have met limited success in providing severely afflicted patients with good neurological and functional recovery. Ghosh and Pearse (2015) suggest that glutaminergic, NA, DA and 5-HT pathways are involved in the initiation and regulation of locomotion and that experimental work provides evidence of the contribution of 5-HT in regulating the rhythm and coordination of movements through the central pattern generator. Experiments with the non-selective 5-HT receptor agonist quipazine show an induction in locomotor-like movements in the presence of the selective 5-HT2 antagonists SB204741 and SB242084. Ghosh and Pearse do not disclose Eletriptan, a 5-HT 1B/1D receptor agonist, used alone without any 5-HT2 antagonists, in treating spinal cord injury and ameliorating locomotor function.

Eletriptan is a triptan drug, first disclosed in WO92/06973 (Pfizer) as 5-HT 1B/1D receptor agonist for the treatment of migraine and for prevention of migraine recurrence. WO92/06973 does not disclose the use of Eletriptan in spinal cord injury and improvement of locomotor function.

SUMMARY

In one aspect, the present disclosure relates to the use of Eletriptan Hydrobromide in the treatment of spinal cord injury and improvement of the locomotive function.

Embodiment 1

The present patent application discloses a Eletriptan Hydrobromide or a pharmaceutical composition thereof for use in the treatment of spinal cord injury.

Embodiment 2

Eletriptan Hydrobromide or a pharmaceutical composition thereof for use in improvement locomotor function after spinal cord injury.

Embodiment 3

Eletriptan Hydrobromide or a pharmaceutical composition thereof for use according to embodiment 1, wherein the spinal cord injury is in acute or subacute phase.

Embodiment 4

Eletriptan Hydrobromide or a pharmaceutical composition thereof for use in the modulation of inflammation associated with spinal cord injury.

Embodiment 5

Eletriptan Hydrobromide or a pharmaceutical composition thereof for use in the protection of vasculature leakage in the spinal cord tissue.

Embodiment 6

Eletriptan Hydrobromide or a pharmaceutical composition thereof for use in the reduction of hemorrhages.

Embodiment 7

Eletriptan Hydrobromide or a pharmaceutical composition thereof for use according to embodiment 6, wherein the hemorrhage is associated with spinal cord injury.

Embodiment 8

Eletriptan Hydrobromide or a pharmaceutical composition thereof for use according to embodiment 7, wherein the spinal cord injury is in acute phase.

Embodiment 9

A method of treating spinal cord injury in a subject in need thereof, comprising administering to the subject a therapeutically effective amount of Eletriptan Hydrobromide or a pharmaceutical composition thereof.

Embodiment 10

The method according to embodiment 9, of Eletriptan Hydrobromide wherein the administration begins starting from 1 hour after injury.

Embodiment 11

The method according to embodiments 9-10, wherein the subject is a warm-blooded vertebrate, preferably a mammal, more preferably a human.

Disclosure/Detailed Description

The present invention concerns the use of Eletriptan Hydrobromide in the treatment of spinal cord injury and improvement of the locomotive function.

As used herein, spinal cord injury (SCI) refers to damage to any part of the spinal cord or nerves resulting from trauma (e.g. a car crash) or from disease or degeneration (e.g. cancer), that causes temporary or permanent changes in its function-Symptoms may include partial or complete loss of motor function, sensory or autonomic function in the parts of the body served by the spinal cord below the level of the injury. The most severe spinal cord injury affects the systems that regulate bowel or bladder control, breathing, heart rate and blood pressure. Most patients with spinal cord injury experience chronic pain.

As used herein, the terms "subject", "host", and "patient", are used interchangeably. As used herein, a subject is preferably a mammal such as a non-primate (e.g., cows, pigs, horses, cats, dogs, rats, mice etc.) or a primate (e.g., monkey and human), most preferably a human.

As used herein, a 'therapeutically effective amount, refers to the amount of agent, (e.g., an amount of Eletriptan Hbr for use in the invention) that provides at least one therapeutic benefit in the treatment or management of the target disease or disorder, when administered to a subject suffering therefrom. Further, a therapeutically effective amount with respect to an agent for use in the invention means that amount of agent alone, or when in combination with other therapies, that provides at least one therapeutic benefit in the treatment or management of the disease or disorder.

"Administering" refers to the physical introduction of an agent to a subject, using any of the various methods and delivery systems known to those skilled in the art. Exemplary routes of administration for the compounds disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intrathecal, intralesional, intracapsular, intradermal, intraperitoneal, subcutaneous, subcapsular, subarachnoid, intraspinal, epidural and intrasternal injection and infusion, as well as in vivo electroporation. In some embodiments, the compound is administered via a non-parenteral route, e.g., orally. Other non-parenteral routes include a topical, epidermal or mucosal route of administration, for example, intranasally, sublingually or topically. Administering can also be performed, for example, once, a plurality of times, and/or over one or more extended periods.

One valuable strategy to accelerate the discovery of new therapeutics for clinical use is the process of finding new uses for existing drugs, i.e. a drug repurposing strategy[20]. Indeed, drugs that originally proved to have a therapeutic effect in one disease could potentially be efficacious in another and as the drugs already undergone preclinical and clinical testing this strategy allows shorter development times, lower costs, lower risks and higher success rates[20,21].

Zebrafish are emerging as a particularly versatile vertebrate model for straightforward and cost-effective drug screenings[20,22-24]. In order to achieve the results disclosed herein, the inventors used a larval zebrafish drug screening platform previously developed their laboratory to identify new molecules with therapeutic properties for SCI indication and identified Eletriptan Hbr with motor recovery properties. Eletriptan Hbr is a FDA-approved drug with highly selective affinity for 5-hydroxytryptamine 1-receptor subtype B/D (5-HT1B/1D) and F (5-HT1F) for the acute treatment of migraine[25,26] and, it is disclosed herein for the first time a new possible therapeutic indication for the use of this molecule. A repurposing strategy was followed, taking advantage of the zebrafish larva (pro-regenerative model) as an in vivo drug screening platform to identify Eletriptan Hbr and then we confirm the conservation of the therapeutic effect in a mice contusion (pro-fibrotic) model by showing its capacity to improve spinal cord functional repair.

Methods

Ethics Statement

All experiments involving animals were performed in with the European Community guidelines accordance (Directive 2010/63/EU), the Portuguese law on animal care (DL 113/2013) and were approved by Instituto de Medicina Molecular Internal Committee (ORBEA) and the Portuguese Animal Ethics Committee (DGAV). All efforts were made to minimize the number of animals used and to decrease suffering of the animals used in the present disclosure.

Animals

Zebrafish SCI Model:

Tg(mnx1:GFP$^{ml2}$), abbreviated as hb9:GFP were maintained and bred in constant conditions, by following standard guidelines for fish care and maintenance protocols[27]. Zebrafish larvae were used in the phenotypic-based screen for SCI.

Mouse SCI Model:

Adult female C57BL/6J mice (8-10 weeks-old; Charles River) were used in this study. The mice were housed three to four per cage and were maintained on a 12-hour light/dark cycle with food and water ad libitum for the duration of the study.

a Phenotypic-Based Screen for SCI

A larval zebrafish phenotypic-based screen was used to screen a pool of compounds from a small molecule library (PHARMAKON 1600-MicroSource Discovery Systems, Inc., USA) as previously described by Diana et al. 2019[28]. Briefly, zebrafish larvae were allowed to develop in EM with 1 µM methylene blue until 5 days-post-fertilization (dpf). At 5dpf, zebrafish larvae spinal cords were transected at the level of the anal pore (Diana et al. 2019). At 1 dpi, larvae were randomly distributed into 6-well plates containing EM+10 mM HEPES and exposed during 24 hours to the chemical compounds added to the medium. At 2 dpi, behavioural assessment was performed using DanioVision™ (Noldus Information Technology, the Netherlands) an automated tracking system for zebrafish larvae. Larvae were allowed to freely swim in a 96-well plate (1 larva/well) with EM+10 mM HEPES and their swimming activity was tracked for 90 minutes, under 10 minutes light-dark cycles (i.e. 3 light cycles and 3 dark cycles). The acquired track data was analysed using the Ethovision X.T. 10 software (Noldus, Wageningen, Netherlands) and only swimming activity obtained in the 3 dark periods were analysed[29].

Contusion Spinal Cord Injury and Post-Operative Care

A moderate-severe contusion-type of injury was performed on adult C57BL/6 female mice (10-12 weeks) with an Infinite Horizon Impactor (PSI)[30]. All surgeries were performed under aseptic conditions. Briefly, under deep anesthesia with Ketamine and Xylazine (120 mg/kg and 16 mg/kg respectively, i.p.) mice received a dorsal laminectomy at the level of 9th thoracic vertebra (T9). After securing the lateral processes of the 8th thoracic vertebra (T8) and 10th thoracic vertebra (T10) with a stainless-steel impactor tip, a controlled force-defined impact at 75 kdyne was delivered to the exposed spinal cord[28,30]. Then, muscle and skin were closed with 4.0 polyglycolic acid (PGA) absorbable sutures (Safil, G1048213). In this study, mice were excluded when the actual displacement value was outside the interval 500-700 µm or if the actual force after impact was >2SD 75 Kdyne. Immediately after injury, mice were injected subcutaneously with 0.5 ml of sterile saline and then daily for 5 days. During this experiment, mice underwent gentle bladder expression twice daily until they were voiding on their own. Weight was monitored daily until 15 days-post-injury (dpi) and then weekly for the duration of the study and a high caloric pellet (Supreme Mini-Treats™ S05478 and S05472) was provided as a dietary supplement since a 10% weight loss was typically observed in this SCI model upon injury.

Drug Treatment in the Mouse SCI Model

The Eletriptan Hbr (Sigma-Aldrich, PZ0011) dosage used were equivalent to the human market dose[31] and all treatment dosages were aliquoted using a coded system to maintain double-blinded measures. This code was only unveiled at the end of all behavioural tests. Mice were randomly distributed to each experimental group (SCI+ Vehicle and SCI+Eletriptan Hbr). Vehicle and Eletriptan Hbr were administered via intraperitoneal injection (i.p.), beginning 1 hour after injury (hpi) and then daily until 15 dpi.

Basso Mouse Scale (BMS) Assessment

Open-field locomotion was assessed with the BMS rating system[30,32]. The open-field used was a round platform with 85 cm in diameter and 30.5 cm high, located in a quiet testing room with normal lighting. The mice were habituated to the testing platform for 5 minutes daily for 2 weeks before surgery. The BMS testing (BMS scoring and subscoring) was performed as previously described[28,30]. Briefly, mice were tested before surgery, to obtain baseline pre-operation locomotion values, where it is expected a maximum S score value. To determine the functional recovery after treatment the BMS score of each mouse was evaluated at 1, 3, 7, 14 dpi and then weekly until the end of the experiments. The evaluation of BMS score and subscore was always performed by two raters who were blind to the treatment groups and scored hindlimb locomotion for 4 minutes per mouse. If the scores differed between raters, the final score taken was the average of both scores.

Acetone Evaporation Assay

An acetone evaporation assay was used to measure the sensitivity to a cold stimulus upon injury[33]. First, mice were habituated to the platform with a wire mesh for 4 minutes and then, one drop of 50 µl of acetone was applied to the hind paw plantar surface using 1 ml syringe. Five trials were performed on each hind paw with an interval of 2 minutes between trials. In each trial, the time spent flicking or licking the hind paw for 60 seconds was measured using a timer and recorded for analysis[34].

Perfusion and Tissue Processing

At the end of behaviour tests, mice were transcardially perfused with 0.9% NaCl, followed by 4% paraformaldehyde (PFA) in 0.1 M phosphate-buffered saline (PBS) at pH 7,4. After an overnight rinse in PBS, spinal cords were cryoprotected for 3 days in 30% sucrose and then frozen in optimal cutting temperature (OCT) compound (Sakura Finetek, USA) in blocks from 3 mm rostral to the injury epicentre to 3 mm caudal (6 mm total). Then, each block was cut on a cryostat in transverse sections (10 µm), mounted on slides in 10 alternating sets, and stored at −20° C. until needed[35].

Immunohistochemistry

For immunohistochemistry in sections, OCT was removed from the cryosections using PBS (30 minutes). Sections were washed with 0.5% PBS-Triton X-100 and blocked in blocking solution (5% goat serum in PBS with 0.1% Triton X-100) for 2 hours at room temperature. Then, spinal cord sections were incubated overnight at 4° C. with anti-GFAP (1:500; ThermoFisher Scientific, 13-0300), anti-PDGFRβ (1:200; Abcam, ab32570), anti-CD31/PECAM-1 (1:100; RD Systems, AF3628), anti-F4/80 (1:500; Abcam, ab6640) and anti-P2Y12 (1:500; AnaSpec AS-55043A) primary antibodies, washed in 0.1% PBS-Triton X-100, PBS and re-incubated overnight at 4° C. with AlexaFluor 568 (1:500; ThermoFisher Scientific, A11011 or A11057), AlexaFluor 488 (1:500; ThermoFisher Scientific, A11006 or A11008) secondary antibodies. For activated microglia quantification, sections were counterstained with DAPI. Sections were then washed in PBS and mounted on a fluorescent mounting medium with DABCO.

FluoroMyelin Green Staining and White Matter Sparing Analysis

To quantify demyelination, one set of sections spaced 100 µm apart and spanning the entire block was stained with FluoroMyelin™ Green (ThermoFisher Scientific, F34651) for 1 hour. Z-stack compositions were acquired in a motorized inverted widefield fluorescence microscope (Zeiss Cell Observer, Carl Zeiss MicroImaging) with 10× magnification. Fiji software was used to measure the cross-sectional area of white matter sparing (WMA) and the total cross-sectional area of the tissue section (TCA), and then the proportional cross-sectional area was calculated (WMA/TCA) from 1100 µm rostral to the injury epicentre to 1100 µm caudal. The epicentre was identified as the section of tissue with the smallest area of fluorescent green stained-white matter in the rim which was identified as the section with the smallest WMA/TCA. The analysis of the lesions were performed through coded sections and by an investigator that was unaware of treatment or outcome groups[36].

Fibrotic Scar Quantification

One set of sections was stained with anti-PDGFRβ and anti-GFAP to outline the border of the fibrotic scar area. Z-stack compositions were acquired in a motorized inverted widefield fluorescence microscope (Zeiss Cell Observer, Carl Zeiss MicroImaging) with 20× magnification. Fiji software was used to manually outline and calculate the PDGFRβ[+] area and total cross-sectional area to thereafter quantify the percentage of fibrotic scar area per total cross-sectional area. The rostral and caudal extents of fibrotic lesion were determined by inspection. Fibrotic lesion length and the extension of PDGFRβ[+] expression was calculated by multiplying the number of sections containing tissue with a fibrotic core or an upregulation of PDGFRβ[+] expression (respectively) by the distance between each section (100 μm).

Activated Microglia Quantification

To quantify the activated microglia one set of spinal cord sections were stained with anti-P2Y12 (a microglia specific marker) and anti-F4/80 (a pan macrophage marker) and counterstained with Z-stack DAPI. Z-stack compositions were acquired in a motorized inverted widefield fluorescence microscope (Zeiss Cell Observer, Carl Zeiss MicroImaging) with 20× magnification. The number of cells were quantified using a custom-made Multichannel Cell counter4TIFF software that calculated the number of F4/80[+] and P2Y12[+] cells after manually setting a threshold value and parameters.

Statistical Analysis

All graphical representations and data analysis from larval zebrafish SCI model were performed using Prism 8 software (GraphPad Software, Inc., San Diego, CA, USA). Statistical tests used were two-tailed. Mean comparisons between the different groups from zebrafish SCI study were performed using unpaired Student's t-test with Welch's correction. Data analysis from mice SCI model were performed using two-way analysis of variance (ANOVA) or repeated measures two-way analysis of variance followed by Bonferroni's post-hoc test using SigmaPlot 14. P value<0.05 was considered significant. All data are expressed as the mean±standard error of the mean (SEM).

Results

Eletriptan Hbr Rescues Locomotor Impairments in a Zebrafish Larval Transected Spinal Cord Injury Model.

To accelerate the discover of potential new therapeutics for spinal cord injury (SCI) we used a phenotypic assay that enabled the screening of a pool of chemical compounds from an FDA approved small molecules library. In this phenotypic-based screen, we blindly administered the chemical compounds (25 μM) at 1 day-post-injury (dpi) and we performed the behavioural assessment 24 hours later (i.e. at 2 dpi) as previously described by Chapela D. et al. 2019. The small molecules were first blindly selected, if there was a statistically significant improvement of total distance moved and/or turn angle parameters, which were chosen as indicators of locomotor function. Then, we narrowed down the selection through defined exclusion criteria (patented or with reported therapeutic indication for SCI; with major reported toxicity or if not able to cross the blood-brain-barrier). Notably, Eletriptan Hbr was one of the most promising candidates identified through this drug discovery platform. Eletriptan Hbr is known as a second generation triptan drug for the acute treatment of migraine with or without aura in human adults and interestingly, showed to rescue locomotor impairments in this zebrafish larval transected spinal cord injury model (FIG. 1A, A'), becoming a promising SCI therapeutic candidate to be tested in a mammal SCI model.

Eletriptan Hbr Improves the Motor Function of Mice with T9 Contusion Type of Injury.

To validate the therapeutic effect of Eletriptan Hbr for SCI indication in a non-regenerative model, it was decided to test its efficacy in a SCI rodent model. Therefore, a contusion type of injury was performed in C57BL/6 female mice, using an Infinite Horizon (IH) Impactor and the Basso Mouse Scale (BMS) test[32] was used to evaluate the loco-motor performance of the animals after injury. First, mice were habituated to the open-field platform and after 15 days they were injured with a moderate-severe T9 contusion (75 kdyne) (FIG. 2A). Immediately after injury and upon bio-mechanical exclusion criteria, mice were randomly distributed to each experimental group (SCI+Vehicle and SCI+Eletriptan Hbr). Treatment dosages (Vehicle or Eletriptan Hbr) were administered via intraperitoneal (i.p.) injection, beginning 1 hour-post-injury (1hpi), and then daily until 15 dpi (FIG. 2A). There were no differences in injury force or displacement applied by the IH Impactor between SCI+Vehicle and SCI+Eletriptan Hbr experimental groups (FIG. 4). For the evaluation of the locomotor recovery upon injury, BMS scores and subscores were measured for 42 days (FIG. 3B-B'). The averages of the BMS scores in the Eletriptan Hbr-treated mice and in the Vehicle-treated mice increased after 1 dpi and reached a plateau between 28-35 dpi and 21-28 dpi, respectively. BMS scores in the Eletriptan Hbr-treated mice were consistently but not significantly higher over time comparing to Vehicle-treated mice (FIG. 3B). Remarkably, one out of thirteen Eletriptan Hbr-treated mice achieved a BMS score of 6 (i.e. showed frequent plantar stepping with some fore-hindlimb coordination) and the remaining twelve achieved a BMS score of 5 (i.e. showed frequent or consistent plantar stepping) at 42 dpi. At the same timepoint, BMS scores of Vehicle-treated mice were 4-5, with three animals out of nine that only achieved an occasional plantar stepping. Moreover, 85% of Eletriptan Hbr-treated mice also showed a frequent plantar stepping with parallel placement of both hindlimb paws at initial contact and 23% displayed a parallel placement of at least one of the hindlimb paws at lift off.

The average BMS subscores were consistently higher in the Eletriptan Hbr-treated mice than in Vehicle-treated mice from 7 to 42 dpi, becoming significantly higher from 35 dpi (FIG. 3B') to 42 dpi (FIG. 3B').

At 42 dpi, eight out of nine Vehicle-treated mice showed a severe trunk instability such as leaning, waddling or near collapse of the hindlimbs and only one animal acquired a mild trunk stability. Furthermore, Eletriptan Hbr-treated mice showed less events that block the walking movement such as spasms and but downs and 46% of the animals from this experimental group acquired a mild trunk stability (FIG. 3C).

Additionally, we also evaluated the bladder dysfunction status, which is a common effect seen after a SCI[3,37]. During the manually bladder expression, we attributed a score from 0 (normal bladder without urine, i.e. animals with void capacity for their own) to 3 (large bladder with a large amount of urine retained). Eletriptan Hbr-treated mice showed statistically significant smaller volumes of retained urine (i.e. smaller scores) at 1 dpi, however this effect was lost after this timepoint, with no differences between experimental groups until the end of the study (FIG. 3D).

Cold allodynia is defined as the hypersensitivity, a painful response to a normally non-noxious cold stimuli that is commonly associated with SCI[33]. In this study, the sensitivity to a cold stimulus was evaluated using the acetone evaporation test at 14 dpi and 42 dpi by quantifying the number of episodes and the duration of the nocifensive responses that were triggered by evaporative cooling. The average of Eletriptan Hbr-treated mice showed a consistently but not a significantly decrease of the cumulative reaction time and a lower number of episodes of the cold hypersensitivity comparing to Vehicle-treated mice (FIG. 3E, E').

Eletriptan Hbr Seems to Prevent Demyelination Near the Terminal Extents of the Lesion To analyse the effect of Eletriptan Hbr on the demyelination status upon injury, the spared white matter area per total cross-sectional area was compared between the experimental groups (SCI+Eletriptan Hbr and SCI+Vehicle), using a FluoroMyelin™ Green fluorescent myelin staining (FIG. 5A). The averages of spared white matter per total cross-sectional area in Eletriptan Hbr-treated mice were not significantly but consistently higher than in the ones treated with Vehicle at lesion epicentre and also over a 700 μm rostrally and caudally from the epicentre of the lesion (FIG. 5B).

The Extension of Increased PDGFR-B Expression Levels is Reduced by Eletriptan Hbr Treatment The fibrotic compartment of the scar is constituted by a subset of PDGFRβ⁺ perivascular cells that creates a core of fibroblast-like cells and a dense deposition of extracellular matrix molecules[37]. Additionally, as it was recently shown that reducing pericyte-derived scarring promotes functional recovery upon spinal cord injury in mice[37] it was decided to analyse the Eletriptan Hbr effect on the fibrotic scar status by evaluating the area and length of the fibrotic scar.

For this analysis, it was performed a double immunohistochemistry with GFAP that allowed to outline the glial limiting border of the scar and with the pericyte marker PDGFRβ to label the fibrotic element of the scar (FIG. 6A-C, 6A'-C', 6A"-C"). With this approach it was possible to outline fibrotic the scar compartment, measuring its area at the lesion epicentre and defining the extension, in length, of the PDGFRβ⁺ lesion core as well as the extension of increased levels of PDGFRβ⁺ immunostaining by comparison with levels of PDGFRβ⁺ staining in Sham-mice. At lesion epicentre, there was no statistically significant differences in the area of fibrotic lesion core between Eletriptan-Hbr treated mice and Vehicle-treated mice at 42 dpi. Although, there were no statistically significant differences in the extension of PDGFRβ⁺ lesion core between Vehicle and Eletriptan Hbr treatment groups, there was a statistically significant reduction in the extension of increased levels of PDGFRβ⁺ immunostaining in mice treated with Eletriptan Hbr comparing to Vehicle-treated mice (FIG. 6D-F).

Eletriptan Hbr Treatment Reduces the Extension of Tissue with Abnormal Numbers of PDGFRβ⁺ Cells that were Associated with Vasculature To infer if increased levels of PDGFRβ⁺ detected on the extremities of the lesion extents were associated with blood vessels we decided to performed a double immunohistochemistry using a pericyte marker PDGFRβ and an endothelial cell marker CD31 (PECAM-1) (FIG. 7). In sections 1000 μm from epicentre, the increased expression of PDGFRβ detected in Vehicle-treated mice and that was reduced in Eletriptan Hbr-treated mice, were associated with CD31⁺ endothelial cells (FIG. 7A-C''').

Microglia is Affected by Eletriptan Hbr

It is known that microglia is crucial to SCI repair. Without microglia, demyelination and pathological MDM infiltrates are enhanced, glial scar formation is disrupted and motor impairments are aggravated[38]. In this context, it was decided to evaluate the effect of Eletriptan Hbr on microglia status upon injury by performing a double immunohistochemistry with P2Y12 (a microglia marker) and F4/80 (a pan macrophage marker). P2Y12⁺ microglia showed ramified morphology with long processes in Sham mice while in Vehicle-treated mice, microglia showed shorter processes that were sparsely detected at lesion epicentre (FIG. 8A-C") In mice treated with Vehicle, few P2Y12⁺ microglia was detected at lesion epicentre and when present microglia was mainly observed in clusters at the lesion margins or in the spared white matter with an amoeboid shape (FIG. 8B, B"; 8C, C"). Eletriptan Hbr treated-mice also showed microglia in clusters with an amoeboid shape and shorter processes at the lesion margins or in the spared white matter but in some sections, near the epicentre or at the epicentre, longer, ramified processes were also observed; feature that was not observed in Vehicle-treated mice (FIG. 8B, B"; 8C, C"). In sections 1000 μm from the epicentre, P2Y12⁺ microglia was present throughout gray and white matter, showing a morphology with some shorter processes and a more reactive shape (mainly at the spinal cord dorsal side) in gray matter in both Vehicle-treated mice and Eletriptan Hbr-treated mice comparing to Sham animals (FIG. 8A, A'; 8B, B"; 8C, C"). There were no statistically significant differences in the number of P2Y12⁺ F4/80⁺ (activated microglia) cells but this number was consistently higher in Eletriptan Hbr-treated mice at 400 μm rostrally and caudally to the epicentre (FIG. 8D).

Spinal cord injury (SCI) has a very complex nature. It is well known that the best system for investigating the potential of compounds that will interfere with complex physiological processes is to evaluate their effect in vivo and zebrafish larva has become a particularly versatile vertebrate model for in vivo phenotypic drug screenings[20,22].

It is herein identified for the first time a promising compound with SCI rescue properties, from a FDA-approved small molecule library using an in vivo larval zebrafish phenotypic-based screen (i.e. using a pro-regenerative model) that was previously established in our lab[28]. Then, we validate and evaluate the conservation of the therapeutic effect of this compound in an in vivo mouse contusion (pro-fibrotic) model of SCI.

From our previously validated zebrafish drug discovery platform we selected Eletriptan Hbr as one of the most promising candidates with spinal cord recovery potential that rescues motor impairments in both total distance moved and turn angle parameters. Importantly, the improvements manifested in total distance and turn angle parameters, not only showed that Eletriptan Hbr rescues the swimming capacity of the SCI larvae as also seemed to improve the motor direction control, respectively.

After the selection of Eletriptan Hbr with this zebrafish approach, this compound was daily administered during the acute and subacute injury phase, beginning 1 hour upon injury (hpi) and then daily until 15 days post injury (dpi), in a T9 contusion mice model. Hence, it is not only confirmed that the Eletriptan Hbr has a conserved effect on the improvement of locomotor behaviour in a pro-fibrotic model as it was also possible to evaluate its effect on the demyelination status, fibrotic scar formation and on the inflammation process at 42 dpi. Importantly, this timepoint constitutes a chronic phase-time in rodents, where reactive astrogliosis and macrophage/microglia-driven inflammation were present.

Notably, Eletriptan Hbr significantly improved the locomotor performance in BMS assessment and showed to improve the mice trunk stability and reduce the number of severe events. Moreover, administration of Eletriptan Hbr consistently but not significantly decreased the cumulative reaction time and lowered the number of episodes of the cold hypersensitivity in the acetone evaporation test, showing that perhaps this compound could diminish cold allodynia in the SCI context. Indeed, despite being used in several studies to measure cold sensitivity, the acetone evaporation test has several limitations, namely, the difficulty to ensure that the exact amount of acetone is applied consistently in each time varying the cold stimulus[33,39]. This method is simple to perform but it only quantifies the magnitude of responses instead of measuring the minimal cold temperature that promotes a response[39]. Sometimes in humans, the extent of functional impairments does not always correlate with tissue damage extension.

Actually, a contusion type of injury often leads to complete motor and sensory loss despite the presence of spared tissue at the injury[40]. Although there was not a statistically significant difference between the treatment groups, Eletriptan Hbr showed to promote a consistently higher myelin preservation near the terminal extents of the lesion.

After SCI, there is a formation of a fibrotic scar that is inhibitory for axonal regrowth and, at the same time, limits immune cells infiltration into the spinal cord parenchyma[41]. Importantly, the moderate inhibition of pericyte-derived scarring not only preserves wound healing and reduces inflammation and reactive astrogliosis as also enables axon regeneration and improves functional recovery[37].

Interestingly, it is disclosed herein that Eletriptan Hbr significantly reduced the extension of increased levels of PDGFR$\beta^+$ immunostaining but not the PDGFR$\beta^+$ fibrotic lesion core area or extension at the epicentre of the lesion. As disclosed in the present patent application, the increased levels of PDGFR$\beta^+$ detected on the extremities of lesion extents were associated to blood vessels, suggesting that Eletriptan Hbr reduced the extent of lesioned tissue with increased numbers of PDGFR$\beta^+$ cells, namely the PDGFR$\beta^+$ associated with CD31+ cells and probably has an effect on the ischemic status.

In response to an injury, microglia becomes activated and enables the regeneration of severed axons through the release of neurotrophic factors and debris removal. However, the secretion of inflammatory cytokines and the production of free radicals might also promote neurotoxicity[38].

Due to the crucial role of Microglia to SCI repair and recovery the inventors decided to investigate the effect of Eletriptan Hbr on the inflammation process. Interestingly, mice treated with Eletriptan Hbr showed to have microglia with a morphology that was more similar to that one characteristic of a moderately activated microglia, showing hypertrophy with shorter processes. Indeed, although microglia was observed with an amoeboid shape in clusters, some mice showed longer, ramified processes in spinal cord sections near the epicentre of the lesion. This was not observed in Vehicle-treated mice where only strongly activated microglia with amoeboid morphology were detected which is characteristic of a robust molecular inflammatory response[9].

Eletriptan Hbr is a serotonin receptor agonist with high affinity for 5-HT1B, 5-HT1D and 5-HT1F receptors, known for its significant clinical efficacy in the treatment of migraine[25]. Remarkably, it is disclosed herein, for the first time, a new indication for Eletriptan Hbr, showing its locomotor recovery properties in two different (a transected pro-regenerative and a contused pro-fibrotic) animal models of SCI. Ultimately, Eletriptan Hbr in a combinatorial therapy with other molecules and associated with engineering approaches and specific time-dependent interventions has a great potential in the context of SCI.

Several features are described hereafter that can each be used independently of one another or with any combination of the other features. However, any individual feature might not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in the specification.

BRIEF DESCRIPTION OF DRAWINGS

For easier understanding of this application, figures are attached in the annex that represent the preferred forms of implementation which nevertheless are not intended to limit the technique disclosed herein.

DESCRIPTION OF THE EMBODIMENTS

Figure 1:
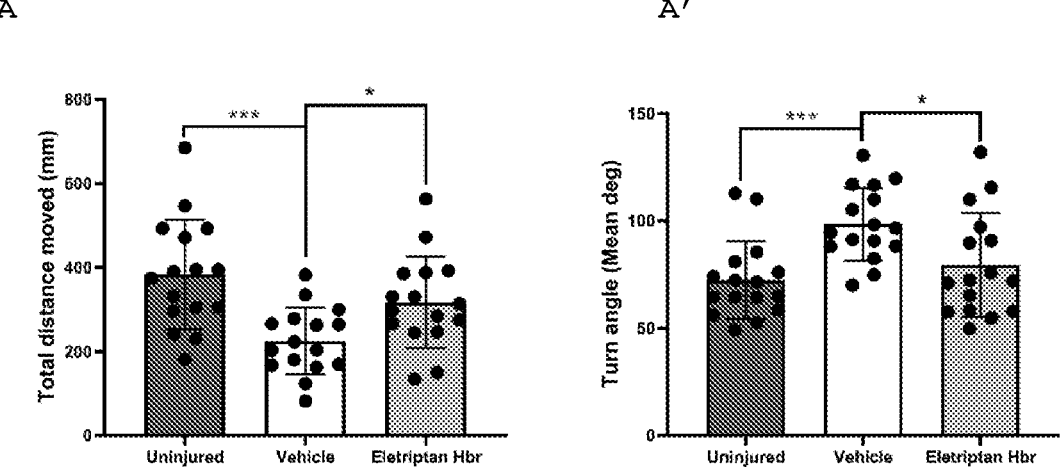
FIG. 1 shows rescue of locomotor impairments by Eletriptan Hbr. Locomotor performance depicted from total distance moved (A) and turn angle (B) in transected zebrafish larvae treated with Eletriptan Hbr, picked from the FDA approved chemical compounds library, as compared to vehicle treated injured larvae (n=16 larvae). Mean±s.e.m. is presented. *p<0.05, ***p<0.001, Student's t-test with Welch's correction.
Figure 2:
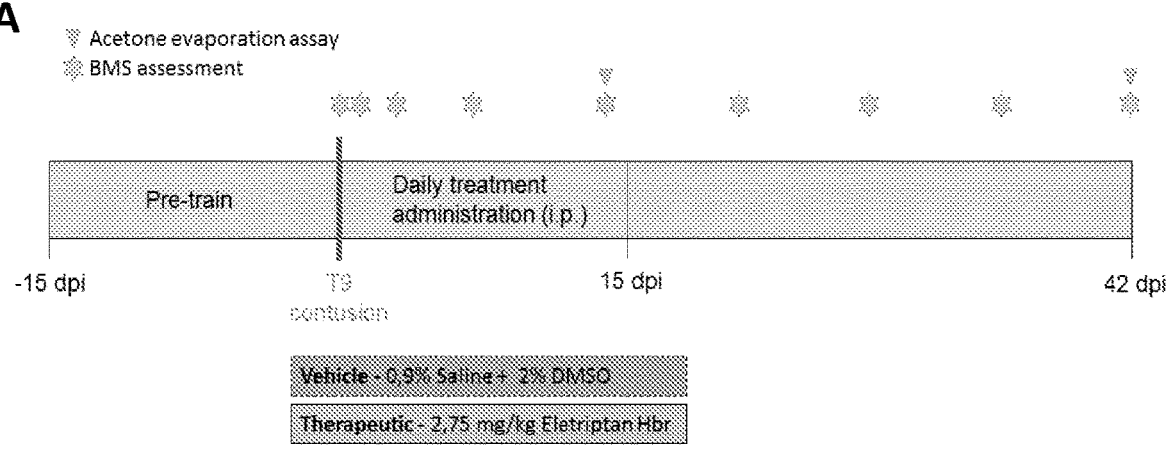
FIG. 2 illustrates experimental design of the efficacy of 15 days of Eletriptan Hbr treatment in a SCI rodent model·shows locomotor recovery of SCI mice with 15 days of treatment upon a T9 contusion-type of injury.
Figure 3:
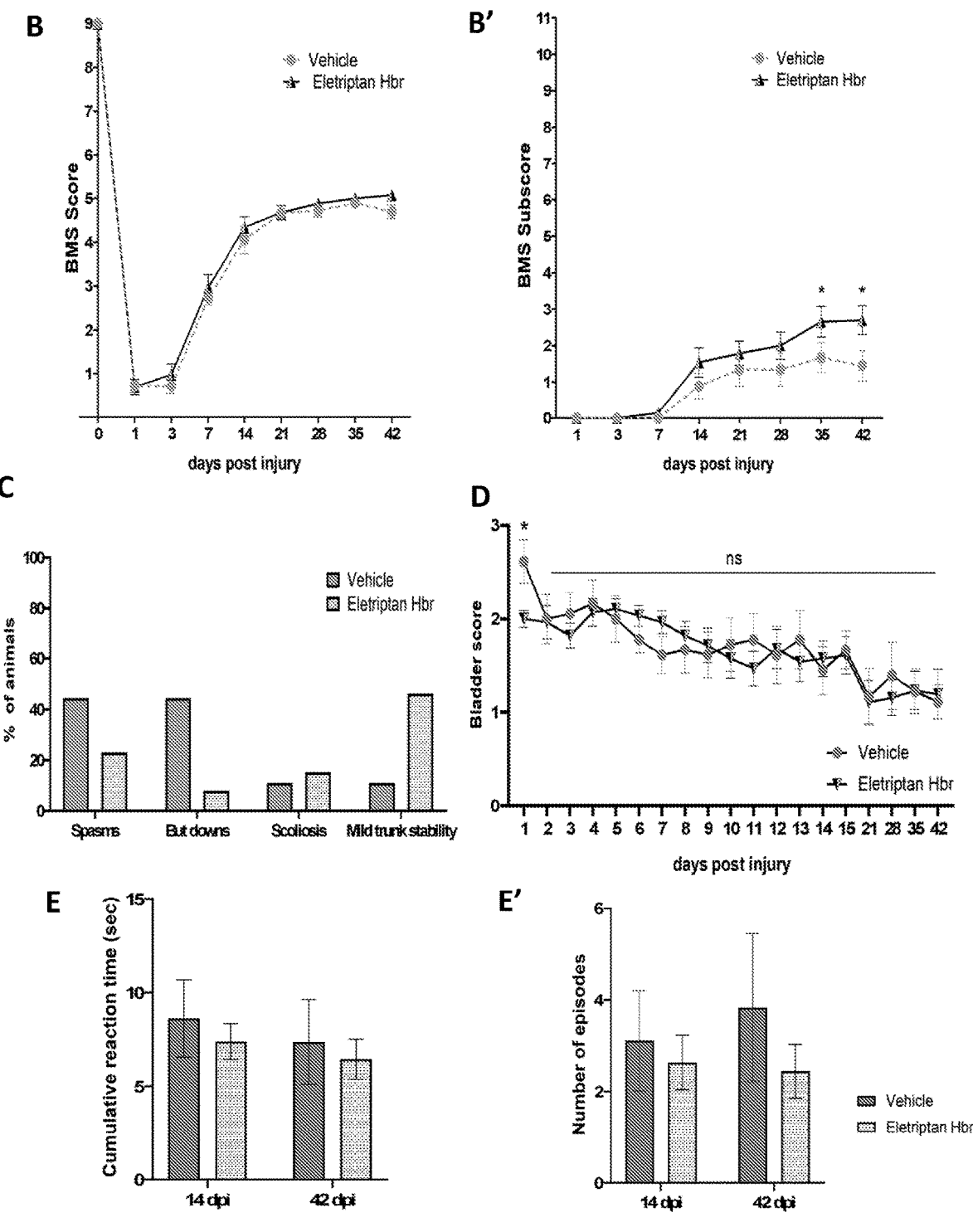
FIG. 3 shows, following to the experimental design of FIG. 2—(B) BMS scores of Eletriptan Hbr-treated mice compared with Vehicle-treated mice from 1 to 42 dpi. n=9 for SCI+Vehicle and n=14 for SCI+Eletriptan Hbr (n=13 for SCI+Eletriptan Hbr after 21 dpi) (B') BMS subscores of Eletriptan Hbr-treated mice compared with the Vehicle-treated mice from 1 to 42 dpi. Mean±s.e.m. is presented. *p<0.05, Two-way repeated measures ANOVA followed by Bonferroni's post-hoc correction. (C) Percentage (%) of animals (42 dpi) from Vehicle-treated mice and Eletriptan Hbr treated-mice with locomotor performance impairments such as spasms, but downs and scoliosis events, as also as with the ability to regain a mild trunk stability, that were observed during BMS testing. n=9 for SCI+Vehicle and n=13 for SCI+Eletriptan Hbr (D) Evaluation of bladder function attributing a score to the amount of urine collected during the manually bladder expression. Mean±s.e.m. is presented. *p<0.05, Two-way repeated measures ANOVA followed by Bonferroni's post-hoc correction. n=9 for SCI+ Vehicle and n=14 for SCI+Eletriptan Hbr (n=13 for SCI+ Eletriptan Hbr after 21 dpi) (E) Cumulative reaction time of nocifensive responses that was triggered by acetone evaporative cooling (E') Number of episodes of the cold hypersensitivity. (E-E') n=8 for SCI+Vehicle and n=11 for SCI+ Eletriptan Hbr at 14 dpi and n=9 for SCI+Vehicle and n=13 for SCI+Eletriptan Hbr at 42 dpi.
Figure 4:
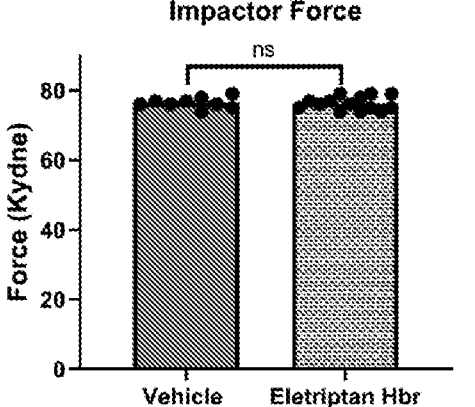
FIG. 4 illustrates Impact force and displacement between experimental groups. (A) Impact force (kdyne) imparted on the spinal cord during SCI (ns—not significant, t student test with Welch's correction). (B) Displacement (μm) of the impactor tip after contact with the spinal cord during SCI (ns—not significant, t student test with Welch's correction). n=9 for Vehicle-treated mice and n=14 for Eletriptan Hbr-treated mice.
Figure 4:
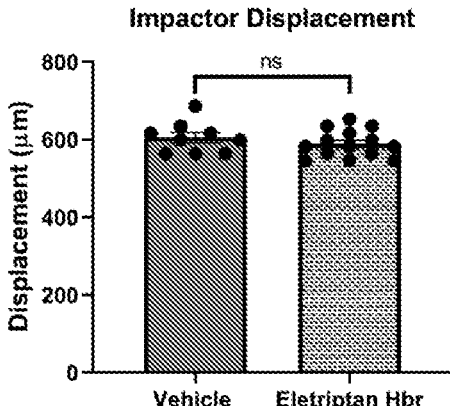
Figure 5:
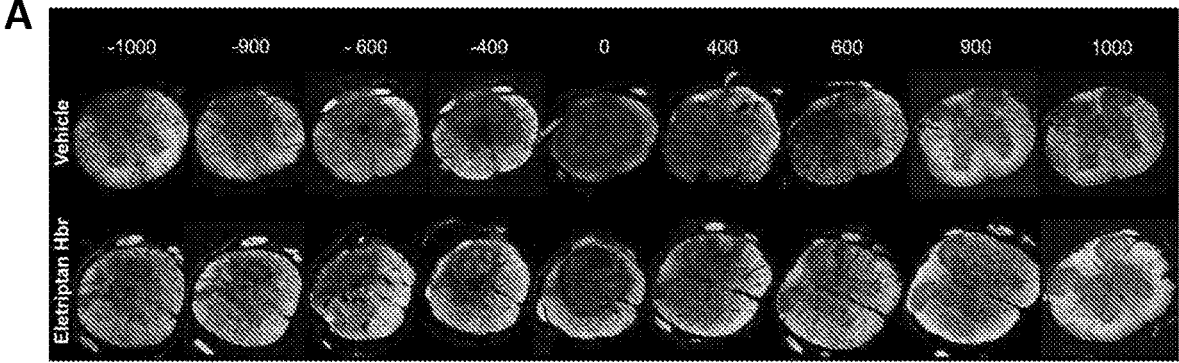
FIG. 5 shows white matter sparing in Vehicle-treated mice and Eletriptan Hbr-treated mice at 42 days upon injury. (A) Representative spinal cord sections of Vehicle-treated mice comparing to Eletriptan Hbr-treated mice stained with FluoroMyelin green. (B) White matter area per total cross section area from epicentre to 1100 µm on the rostral and caudal sides in Vehicle-treated mice and in Eletriptan Hbr-treated mice. Two-way ANOVA followed by Bonferroni post hoc correction. n=8 for SCI+Vehicle and n=12 for SCI+Eletriptan Hbr.
Figure 5:
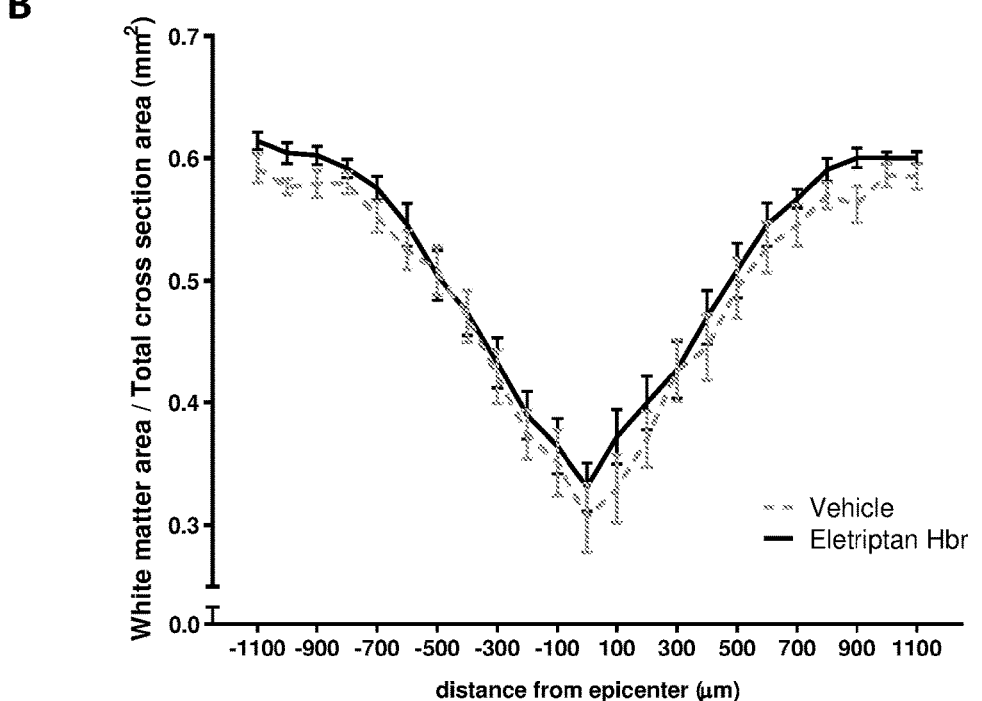
Figure 6:
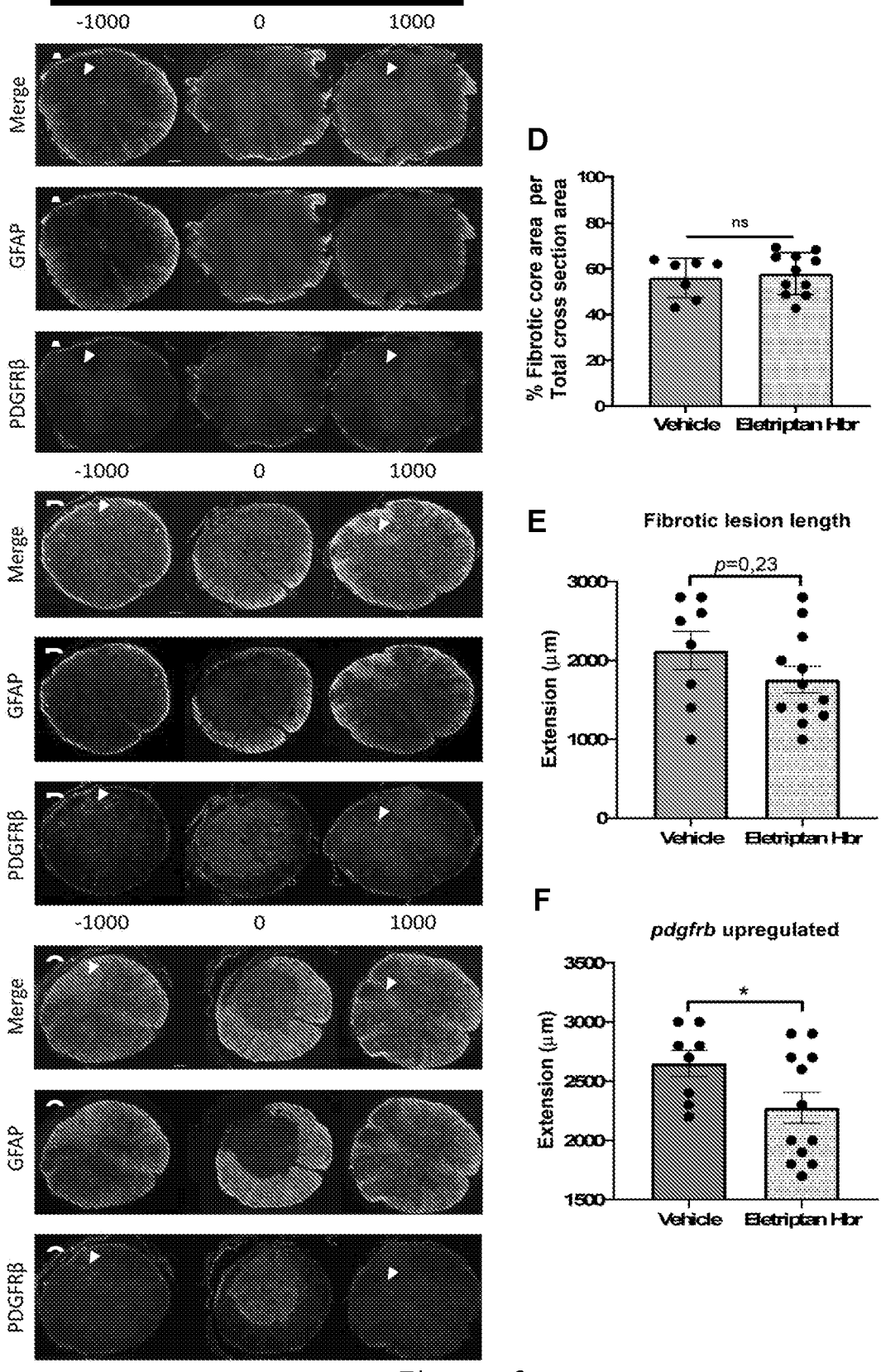
FIG. 6 shows evaluation of the fibrotic scar at 42 dpi. (A-C") Immunofluorescence representative images of spinal cord sections showing GFAP$^+$ astrocytes (green) (A'-C'), PDGFRβ$^+$ pericytes/fibroblasts (magenta) (A"-C") and the merge channel (A-C) at the lesion epicenter and 1000 µm rostrally and caudally to the epicentre in sham, vehicle-treated mice and Eletriptan Hbr-treated mice, respectively. White arrowheads show the PDGFRβ expression at the spinal cord dorsal side at 1000 µm rostrally and caudally to the epicenter. (D-F) Graphical representations of the percentage of fibrotic lesion core area per total cross-sectional area (D), fibrotic lesion length (E) and the extension (in length) of lesion tissue where is visible an upregulation of PDGFRβ expression (F) in Vehicle-treated mice (n=8) and in Eletriptan Hbr-treated mice (n=12). *p<0.05, Student's t-test with Welch's correction. Scale bar: 150 µm.
Figure 7:
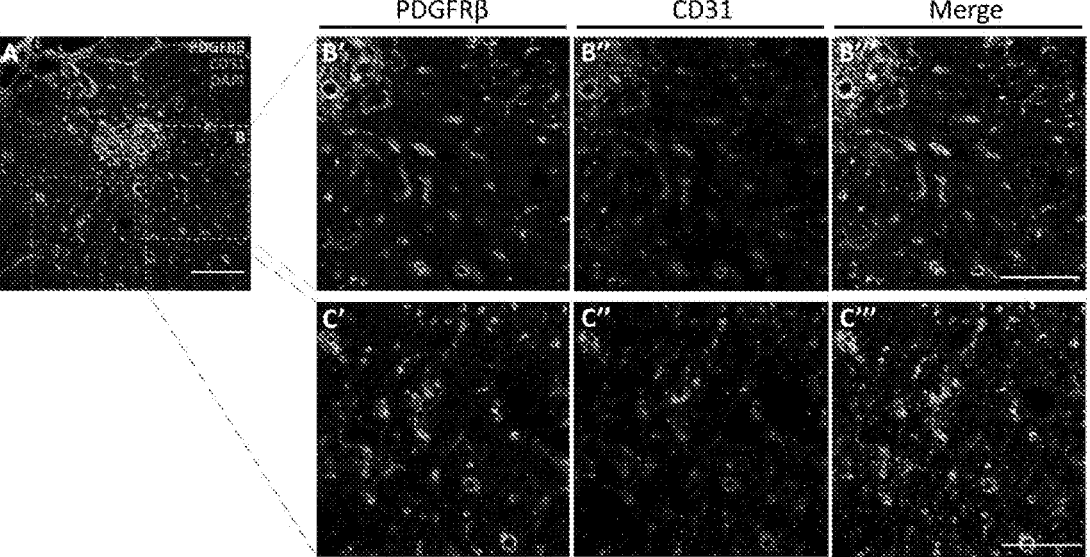
FIG. 7 shows PDGFRβ$^+$ cells associated with the vasculature in a Vehicle-spinal cord section at 1000 µm from epicenter. (A) Immunofluorescence representative image of a spinal cord section showing PDGFRβ$^+$ pericytes/fibroblasts (green), CD31$^+$ endothelial cells (magenta) and the merge channel with DAPI at 42 dpi. (B'-B''') Zoom in spinal cord section images of the ROI area B. (C'-C''') Zoom in spinal cord section images of the ROI area C. White arrowheads show the presence of PDGFRβ$^+$ associated to CD31+ cells . . . Scale bar: 150 µm (A) and 100 µm (B'-C''').
Figure 8:
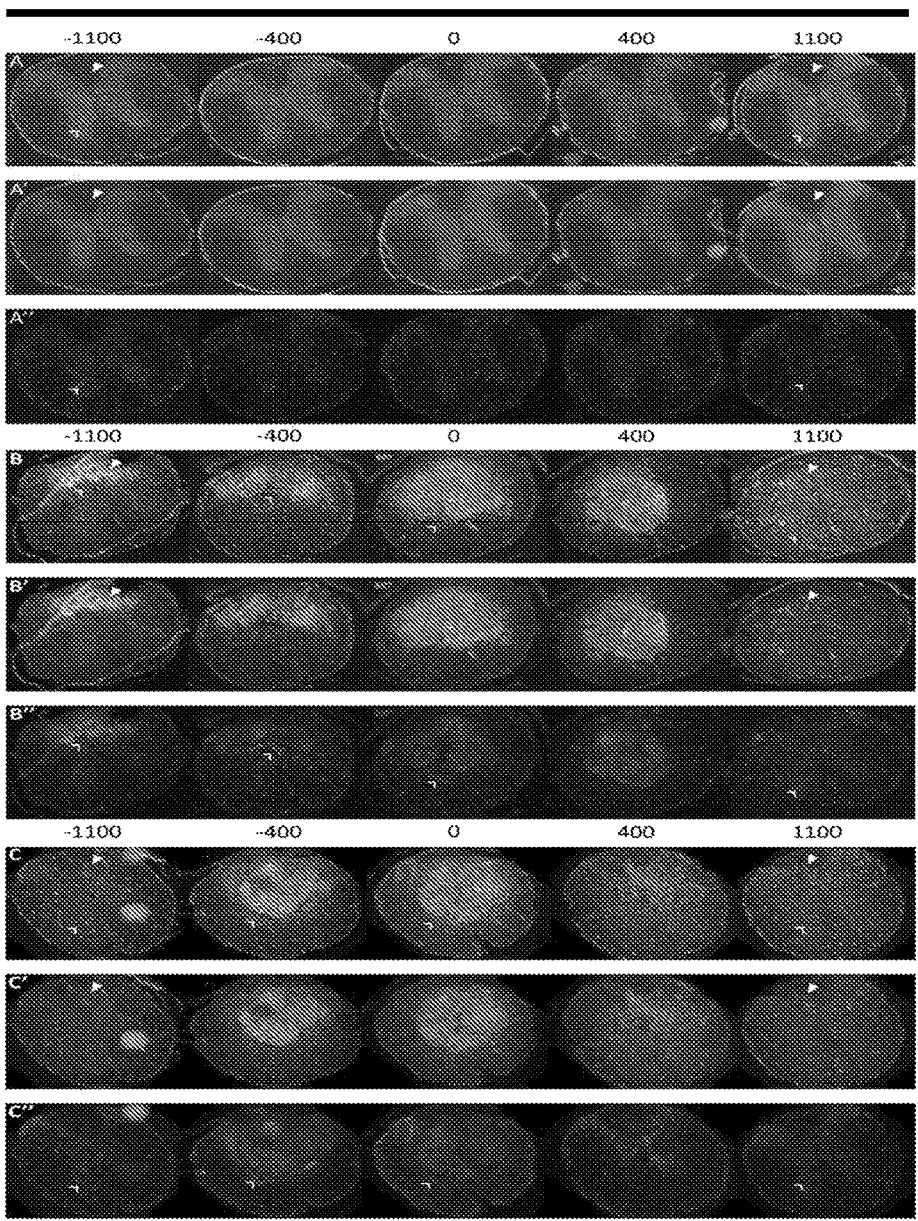
FIG. 8 shows inflammatory response at 42 dpi. (A-C") Immunofluorescence representative images of spinal cord sections showing F4/80$^+$ macrophages (green) (A'-C'), P2Y12$^+$ microglia (magenta) (A"-C") and the merge channel (A-C) at the lesion epicenter, 400 and 1100 µm rostrally and caudally to the epicentre in sham, vehicle-treated mice and Eletriptan Hbr-treated mice, respectively. White arrowheads show the F4/80 expression and white half frames show the P2Y12 expression at the spinal cord dorsal side at 1100 µm rostrally and caudally to the epicentre. (D) Counts of P2Y12$^+$ F4/80$^+$ activated microglia cells. n=8 for SCI+Vehicle and n=12 for SCI+Eletriptan Hbr Statistical analysis was performed using a one-way ANOVA followed by a Bonferroni's post hoc test Scale bar: 150 µm
Figure 8:
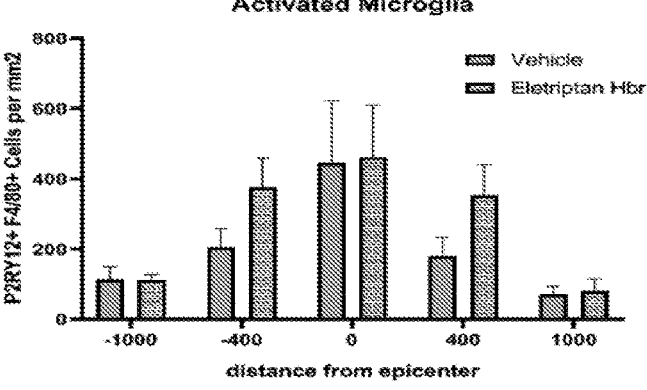

Now, preferred embodiments of the present application will be described in detail, however, these are not intended to limit the scope of this application.

Embodiment 1

The present patent application discloses a Eletriptan Hydrobromide or a pharmaceutical composition thereof for use in the treatment of spinal cord injury.

Embodiment 2

Eletriptan Hydrobromide or a pharmaceutical composition thereof for use in improvement locomotor function after spinal cord injury.

Embodiment 3

Eletriptan Hydrobromide or a pharmaceutical composition thereof for use according to embodiment 1, wherein the spinal cord injury is in acute phase.

Embodiment 4

Eletriptan Hydrobromide or a pharmaceutical composition thereof for use in the modulation of inflammation associated with spinal cord injury.

Embodiment 5

Eletriptan Hydrobromide or a pharmaceutical composition thereof for use in the protection of leakage of the vessels in the spinal blood barrier.

Embodiment 6

Eletriptan Hydrobromide or a pharmaceutical composition thereof for use in the reduction of hemorrhages.

Embodiment 7

Eletriptan Hydrobromide or a pharmaceutical composition thereof for use according to embodiment 6, wherein the hemorrhage is associated with spinal cord injury.

Embodiment 8

Eletriptan Hydrobromide or a pharmaceutical composition thereof for use according to embodiment 7, wherein the spinal cord injury is in acute phase.

Embodiment 9

A method of treating spinal cord injury in a subject in need thereof, comprising administering to the subject a therapeutically effective amount of Eletriptan Hydrobromide or a pharmaceutical composition thereof.

Embodiment 10

The method according to embodiment 9, wherein the administration f Eletriptan Hydrobromide begins starting from 1 hour after injury.

Embodiment 11

The method according to embodiments 9-10, wherein subject is a warm-blooded vertebrate, preferably a mammal, more preferably a human.

Suitable unit forms of administration of pharmaceutical compositions comprising Eletriptan Hbr include, as non-limiting examples, forms administered orally and forms administered via a parenteral route, non-limiting examples of which including inhalation, subcutaneous administration, intramuscular administration, intravenous administration and intradermal administration.

In some embodiments, pharmaceutical compositions for oral administration can be in the form of tablets, pills, powders, hard gelatine capsules, soft gelatine capsules, and/or granules. In some embodiments of such pharmaceutical compositions, a compound of the disclosure and/or a pharmaceutically acceptable salt of a compound of the disclosure is (or are) mixed with one or more inert diluents, non-limiting examples of which including starch, cellulose, sucrose, and lactose, silica. In some embodiments, such pharmaceutical compositions may further comprise one or more substances other than diluents, such as (as non-limiting examples), lubricants, coloring agents, coatings, or varnishes.

In the present specification, embodiments of the invention have been described with reference to numerous specific details that may vary to from implementation implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

REFERENCES

1 Kjell, J. & Olson, L. Rat models of spinal cord injury: from pathology to potential therapies. Dis Model Mech 9, 1125-1137, doi: 10.1242/dmm. 025833 (2016).

2 Boutonnet, M., Laemmel, E., Vicaut, E., Duranteau, J. & Soubeyrand, M. Combinatorial therapy with two pro-coagulants and one osmotic agent reduces the extent of the lesion in the acute phase of spinal cord injury in the rat. Intensive Care Med Exp 5, 51, doi: 10.1186/s40635-017-0164-z (2017).

3 Donovan, J. & Kirshblum, S. Clinical Trials in Traumatic Spinal Cord Injury. Neurotherapeutics 15, 654-668, doi: 10.1007/s13311-018-0632-5 (2018).

4 Duncan, G. J. et al. Locomotor recovery following contusive spinal cord injury does not require oligodendrocyte remyelination. Nat Commun 9, 3066, doi: 10.1038/s41467-018-05473-1 (2018).

5 Zhou, X., He, X. & Ren, Y. Function of microglia and macrophages in secondary damage after spinal cord injury. Neural Regen Res 9, 1787-1795, doi: 10.4103/1673-5374.143423 (2014).

6 Yilmaz, T. & Kaptanoğlu, E. Current and future medical therapeutic strategies for the functional repair of spinal cord injury. World J Orthop 6, 42-55, doi: 10.5312/wjo.v6.i11.42 (2015).

7 Picoli, C. C. et al. Pericytes Act as Key Players in Spinal Cord Injury. Am J Pathol 189, 1327-1337, doi: 10.1016/j.ajpath.2019.03.008 (2019).

8 O'Shea, T. M., Burda, J. E. & Sofroniew, M. V. Cell biology of spinal cord injury and repair. J Clin Invest 127, 3259-3270, doi: 10.1172/JCI90608 (2017).

9 Gaudet, A. D. & Fonken, L. K. Glial Cells Shape Pathology and Repair After Spinal Cord Injury. Neurotherapeutics 15, 554-577, doi: 10.1007/s13311-018-0630-7 (2018).

10 Hausmann, O. N. Post-traumatic inflammation following spinal cord injury. Spinal Cord 41, 369-378, doi: 10.1038/sj.sc.3101483 (2003).

11 Bradbury, E. J. & Burnside, E. R. Moving beyond the glial scar for spinal cord repair. Nat Commun 10, 3879, doi: 10.1038/s41467-019-11707-7 (2019).

12 Orr, M. B. & Gensel, J. C. Spinal Cord Injury Scarring and Inflammation: Therapies Targeting Glial and Inflam-matory Responses. Neurotherapeutics 15, 541-553, doi: 10.1007/s13311-018-0631-6 (2018).

13 Cregg, J. M. et al. Functional regeneration beyond the glial scar. Exp Neurol 253, 197-207, doi: 10.1016/j.expneurol.2013.12.024 (2014).

14 Zhang, B. et al. Reducing age-dependent monocyte-derived macrophage activation contributes to the therapeutic efficacy of NADPH oxidase inhibition in spinal cord injury. Brain Behav Immun 76 139-150, doi: 10.1016/j.bbi.2018.11.013 (2019).

15 Keirstead, H. S. et al. Human embryonic stem cell-derived oligodendrocyte progenitor cell transplants remyelinate and restore locomotion after spinal cord injury. J Neurosci 25, 4694-4705, doi: 10.1523/JNEURO-SCI.0311-05.2005 (2005).

16 McTigue, D. M. & Tripathi, R. B. The life, death, and replacement of oligodendrocytes in the adult CNS. J Neurochem 107, 1-19, doi: 10.1111/j.1471-4159.2008.05570.x (2008).

17 Bellver-Landete, V. et al. Microglia are an essential component of the neuroprotective scar that forms after spinal cord injury. Nat Commun 10, 518, doi: 10.1038/s41467-019-08446-0 (2019).

18 Anderson, M. A. et al. Astrocyte scar formation aids central nervous system axon regeneration. Nature 532, 195-200, doi: 10.1038/nature17623 (2016).

19 Courtine, G. & Sofroniew, M. V. Spinal cord repair: advances in biology and technology. Nat Med 25, 898-908, doi: 10.1038/s41591-019-0475-6 (2019).

20 Hall, c. J. et al. Repositioning drugs for inflammatory disease-fishing for new anti-inflammatory agents. Dis Model Mech 7, 1069-1081, doi: 10.1242/dmm. 016873 (2014).

21 Buckley, C. E. et al. Drug reprofiling using zebrafish identifies novel compounds with potential pro-myelina-tion effects. Neuropharmacology 59, 149-159, doi: 10.1016/j.neuropharm.2010.04.014 (2010).

22 Rennekamp, A. J. & Peterson, R. T. 15 years of zebrafish chemical screening. Curr Opin Chem Biol 24, 58-70, doi: 10.1016/j.cbpa.2014.10.025 (2015).

23 Early, J. J. et al. An automated high-resolution in vivo screen in zebrafish to identify chemical regulators of myelination. Elife 7, doi: 10.7554/eLife.35136 (2018).

24 MacRae, C. A. & Peterson, R. T. Zebrafish as tools for drug discovery. Nat Rev Drug Discov 14, 721-731, doi: 10.1038/nrd4627 (2015).

25 Capi, M. et al. Eletriptan in the management of acute migraine: an update on the evidence for efficacy, safety, and consistent response. Ther Adv Neurol Disord 9, 414-423, doi: 10.1177/1756285616650619 (2016).

26 Tepper, S. J., Rapoport, A. M. & Sheftell, F. D. Mechanisms of action of the 5-HT1B/1D receptor agonists. Arch Neurol 59, 1084-1088, doi: 10.1001/archneur.59.7.1084 (2002).

27 Westerfield, M. The Zebrafish Book: A Guide for the Laboratory Use of Zebrafish (*Brachydanio rerio*). (2000).

28 Chapela, D. et al. A zebrafish drug screening platform boosts the discovery of novel therapeutics for spinal cord injury in mammals. Sci Rep 9, 10475, doi: 10.1038/s41598-019-47006-w (2019).

29 de Esch, C. et al. Locomotor activity assay in zebrafish larvae: influence of age, strain and ethanol. Neurotoxicol Teratol 34, 425-433, doi: 10.1016/j.ntt.2012.03.002 (2012).

30 Tep, C. et al. Oral administration of a small molecule targeted to block proNGF binding to p75 promotes myelin sparing and functional recovery after spinal cord injury. J Neurosci 33, 397-410, doi: 10.1523/JNEUROSCI.0399-12.2013 (2013).

31 Nair, A. B. & Jacob, S. A simple practice guide for dose conversion between animals and human. J Basic Clin Pharm 7, 27-31, doi: 10.4103/0976-0105.177703 (2016).

32 Basso, D. M. et al. Basso Mouse Scale for locomotion detects differences in recovery after spinal cord injury in five common mouse strains. J Neurotrauma 23, 635-659, doi: 10.1089/neu.2006.23.635 (2006).

33 Deuis, J. R., Dvorakova, L. S. & Vetter, I. Methods Used to Evaluate Pain Behaviors in Rodents. Front Mol Neurosci 10, 284, doi: 10.3389/fnmol.2017.00284 (2017).

34 Golden, J. P. et al. RET signaling is required for survival and normal function of nonpeptidergic nociceptors. J Neurosci 30, 3983-3994, doi: 10.1523/JNEURO-SCI.5930-09.2010 (2010).

35 Ma, M., Basso, D. M., Walters, P., Stokes, B. T. & Jakeman, L. B. Behavioral and histological outcomes following graded spinal cord contusion injury in the C57Bl/6 mouse. Exp Neurol 169, 239-254, doi: 10.1006/exnr.2001.7679 (2001).

36 Hoschouer, E. L., Finseth, T., Flinn, S., Basso, D. M. & Jakeman, L. B. Sensory stimulation prior to spinal cord injury induces post-injury dysesthesia in mice. J Neurotrauma 27, 777-787, doi: 10.1089/neu.2009.1182 (2010).

37 Dias, D. O. et al. Reducing Pericyte-Derived Scarring Promotes Recovery after Spinal Cord Injury. Cell 173, 153-165.e122, doi: 10.1016/j.cell.2018.02.004 (2018).

38 Brennan, F. H., Hall, J. C. E., Guan, Z. & P. G., P. Microglia limit lesion expansion and promote functional recovery after spinal cord injury in mice. Cold Spring Harbor Laboratory, doi:https://doi.org/10.1101/410258 (2018).

39 Brenner, D. S., Golden, J. P. & Gereau, R. W. A novel behavioral assay for measuring cold sensation in mice. PLOS One 7, e39765, doi: 10.1371/journal.pone.0039765 (2012).

40 Oudega, M. Molecular and cellular mechanisms underlying the role of blood vessels in spinal cord injury and repair. Cell Tissue Res 349, 269-288, doi: 10.1007/s00441-012-1440-6 (2012).

41 Zhu, Y. et al. Hematogenous macrophage depletion reduces the fibrotic scar and increases axonal growth after spinal cord injury. Neurobiol Dis 74, 114-125, doi: 10.1016/j.nbd.2014.10.024 (2015).

42 Khennouf, L. et al. Active role of capillary pericytes during stimulation-induced activity and spreading depolarization. Brain 141, 2032-2046, doi: 10.1093/brain/awy143 (2018).

43 Li, Y. et al. Pericytes impair capillary blood flow and motor function after chronic spinal cord injury. Nat Med 23, 733-741, doi: 10.1038/nm.4331 (2017).

The invention claimed is:

1. A method of treating spinal cord injury comprising a contusion in a subject in need thereof, comprising administering to the subject a therapeutically effective amount of Eletriptan Hydrobromide or a pharmaceutical composition thereof.

2. The method according to claim 1, wherein the administration of Eletriptan Hydrobromide begins at 1 hour after injury.

3. The method according to claim 1, wherein the subject is a human.

4. The method according to claim 1, wherein the subject is a mammal.

5. The method according to claim 1, wherein the spinal cord injury is in an acute phase.

6. The method according to claim 1, wherein the spinal cord injury is in a sub-acute phase.

7. The method according to claim 1, wherein the treatment comprises a reduction in a hemorrhage associated with the spinal cord injury.

8. The method according to claim 1, wherein the treatment comprises modulation of the inflammatory process associated with the spinal cord injury.

9. The method according to claim 1, wherein the treatment comprises an improvement in locomotive function of the subject.

10. The method according to claim 9, wherein the treatment comprises an acute injury.

11. A method of protecting from microvascular leakage in a spinal cord tissue of a subject in need thereof, comprising administering to the subject a therapeutically effective amount of Eletriptan Hydrobromide or a pharmaceutical composition thereof.

* * * * *